US00PP11445P

United States Patent [19]

Trees

[11] Patent Number: Plant 11,445

[45] Date of Patent: Jul. 11, 2000

[54] NEW GUINEA IMPATIENS PLANT NAMED 'BFP-865'

[75] Inventor: Scott C. Trees, Nipomo, Calif.

[73] Assignee: Ball Floraplant, a Division of Ball Horticultural Co., West Chicago, Ill.

[21] Appl. No.: 09/113,131

[22] Filed: Jul. 9, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 8,112 1/1993 Dehan ..... Plt./318
P.P. 10,304 3/1998 Kientzler ..... Plt./318

*Primary Examiner*—Howard J. Locker
*Assistant Examiner*—Wendy A. Baker
*Attorney, Agent, or Firm*—C. A. Whealy

[57] ABSTRACT

A new and distinct cultivar of New Guinea Impatiens plant named 'BFP-865', characterized by its lavender-colored flowers; compact, upright and mounded plant habit; good basal branching; and dark green leaves.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the cultivar name BFP-865.

The new New Guinea Impatiens is a product of a planned breeding program conducted by the Inventor in Arroyo Grande, Calif. The objective of the breeding program was to develop new cultivars with excellent basal branching, upright and medium growth habit, numerous large flowers, and interesting flower and foliage colors.

The new New Guinea Impatiens originated from a cross made by the Inventor of the *Impatiens hawkeri* cultivar Samoa (disclosed in U.S. Plant Pat. No. 8,422) as the male, or pollen parent, with the *Impatiens hawkeri* cultivar Prepona (disclosed in U.S. Plant Pat. No. 9,150) as the female, or seed parent. The cultivar BFP-865 was discovered and selected by the Inventor as a flowering plant within the progeny of the stated cross in a controlled environment in Arroyo Grande, Calif., on Sep. 15, 1996. Plants of the new New Guinea Impatiens differ from plants of both parents primarily in flower petal color, since 'Samoa' has white flowers with a pink blush and 'Prepona' has bright red flowers.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'BFP-865'. These characteristics in combination distinguish 'BFP-865' as a new and distinct cultivar:

1. Lavender-colored flowers.
2. Compact, upright and mounded plant habit.
3. Good basal branching.
4. Dark green leaves.

The new New Guinea Impatiens can be compared to the cultivar, Bora Bora (disclosed in U.S. Plant Pat. No. 8,421). However, in side-by-side comparisons conducted by the Inventor in Arroyo Grande, Calif., plants of the new New Guinea Impatiens differ from plants of the cultivar Bora Bora in the following characteristics:

1. Plants of the new New Guinea Impatiens are more compact and have shorter internodes than plants of the cultivar Bora Bora.
2. Plants of the new New Guinea Impatiens have slightly larger leaves than plants of the cultivar Bora Bora.
3. Leave of plants of the new New Guinea Impatiens are smoother and less shiny than leaves of plants of the cultivar Bora Bora.
4. Flower color of plants of the new New Guinea Impatiens is lighter and more blue than the flower color of plants of the cultivar Bora Bora.

A detailed comparison of plants of the cultivar BFP-865 and the cultivar Bora Bora appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'BFP-865'. Flower and foliage colors in the photograph may appear different from the actual colors due to light reflectance.

DETAILED BOTANICAL DESCRIPTION

The cultivar BFP-865 has not been observed under all possible environmental conditions. The phenotype may vary somewhat with variations in environment such as temperature and light intensity, without, however, any variance in genotype. The following observations, measurements and comparisons describe plants grown 10-cm pots in Arroyo Grande, Calif., under commercial practice in a glass-covered greenhouse with day temperatures about 22° C. and night temperatures about 18° C.

In the following description, color references are made to The Royal Horticultural Society Colour chart except where general terms of ordinary dictionary significance are used.

Botanical classification: *Impatiens hawkeri* cultivar BFP-865.

Parentage:

*Male parent.*—*Impatiens hawkeri* cultivar Samoa, disclosed in U.S. Plant Pat. No. 8,422.

*Female parent.*—*Impatiens hawkeri* cultivar Prepona, disclosed in U.S. Plant Pat. No. 9,150.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous, fine, freely branching.

Plant description:

*Plant form.*—Compact, upright and mounded.

*Growth and branching habit.*—Moderately vigorous. Good basal branching with about six lateral branches at the base, dense and bushy growth. Appropriate for 10 and 12.5-cm. containers.

*Crop time.*—About ten weeks are required to produce a finished flowering plant in a 10-cm container from a rooted cutting.

*Plant height.*—About 9.6 cm.

*Lateral branches.*—Length: About 6.3 cm. Diameter: About 5.5 mm. Internode length: About 4 cm. Color: 183B.

*Foliage description.*—Leaves simple, generally symmetrical, abundant, in whorls or opposite. Quantity of leaves per lateral branch: About 10. Length: About 8.2 cm. Width: About 3.5 cm. Shape: Lanceolate with acuminate apex, attenuate base and serrate/ciliate margin. Texture: Smooth, dull, slightly pubescent. Color: Young foliage, upper surface: 146A. Young foliage, lower surface: 146D. Fully expanded foliage, upper surface: 147A. Fully expanded foliage, lower surface: 147C. Midvein, upper surface: Towards base, 53C, gradually fading to light green, 154D, towards apex. Midvein, lower surface: 53C. Petiole: Length: About 2 cm. Diameter: About 3 mm. Color: 184A.

Flower description:

*Flower type and habit.*—Lavender-colored flowers. Freely and continuously flowering. Flowers arise from leaf axils. Usually about seven flowers and flower buds per lateral branch. Flowers positioned mostly above the foliage and typically face upright. Flowers generally slightly cupped and rounded to rectangular. Flowers persistent.

*Flowering season.*—Year-round under greenhouse conditions. In the garden, flowering is continuous from spring until fall.

*Flower longevity.*—About one week.

*Flower size.*—Diameter: About 6.3 cm. Depth: About 1.5 cm.

*Flower buds.*—Length: About 2.4 cm. Diameter: About 1.6 cm. Shape: Ellipsoidal. Color: 78A.

*Petals.*—Quantity: Five, overlapping. Length: About 3.3 cm. Width: About 4.2 cm. Shape: Obcordate with emarginate apex, attenuate base and entire margin. Base of upper petal is typically broader. Texture: Smooth, iridescent. Color: Upper petals, upper surface: 81B fading to 81C; 60C at base; midvein, 81A. Lower petals, upper surface: 81B fading to 81C; 60C at base. Upper petals, lower surface; Closest to 84B; 60C where sepal is fused to petal. Lower petals, lower surface: Closest to 84B; midvein, 81B.

*Spur.*—Length: About 5 cm. Shape: Narrow and curved. Color: 53A.

*Peduncles.*—Length: About 5.3 cm. Angle: About 45°. Strength: Strong. Color: 53A.

*Reproductive organs.*—Androecium: Stamen number: Five, anthers fused, filaments free. Anther shape: Obovate. Anther color: 8D. Amount of pollen: Moderate. Pollen color: 13D. Gynoecium: Five-loculate fused. Stigma color: Clear. Ovary color: 144A.

Disease resistance: Under commercial conditions, resistance to pathogens has not been observed.

Seed development: Seed production has not been observed.

CHART A

| CHARACTERISTIC | 'BFP-865' | 'BORA BORA' |
|---|---|---|
| PLANT HEIGHT | About 9.6 cm | About 10.5 cm |
| LATERAL BRANCH LENGTH | About 6.3 cm | About 6.8 cm |
| LATERAL BRANCH DIAMETER | About 5.5 mm | About 6.5 mm |
| INTERNODE LENGTH | About 4 cm | About 5 cm |
| LEAF LENGTH | About 8.2 cm | About 7.7 cm |
| LEAF WIDTH | About 3.5 cm | About 3 cm |
| LEAF TEXTURE | Smooth, dull | Rugose, shiny |
| FLOWER ASPECT | Slightly cupped | Flat |
| FLOWER DIAMETER | About 6.3 cm | About 6 cm |
| PETAL LENGTH | About 3.3 cm | About 3.7 cm |
| PETAL WIDTH | About 4.2 cm | About 3.6 cm |
| PETAL COLOR, UPPER SURFACE | 81B fading to 81C; 60C at base; midvein 81A | Darker and more red than 80A |
| PETAL COLOR, LOWER SURFACE | Closest to 84B; 60C where sepal is fused to petal | 78A/80A; 63B at base |
| PEDUNCLE LENGTH | About 5.3 cm | About 5.8 cm |
| PEDUNCLE COLOR | 53A | 53C |

It is claimed:

1. A new and distinct cultivar of New Guinea Impatiens plant named 'BFP-865', as illustrated and described.

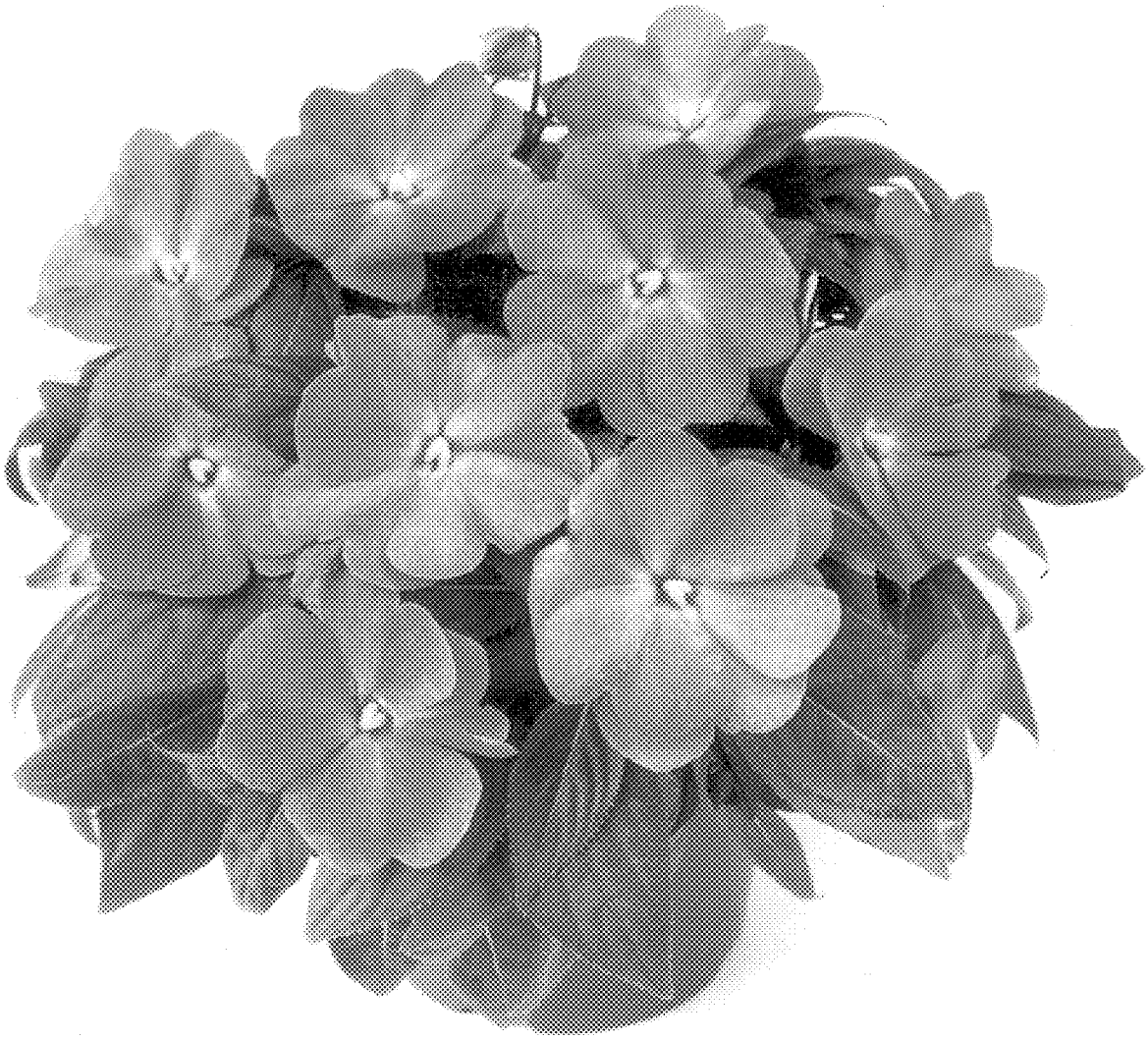

* * * * *